United States Patent [19]

Müller-Kuhrt et al.

[11] Patent Number: 5,646,179
[45] Date of Patent: Jul. 8, 1997

[54] γ-PYRONES, γ-PYRIDONES, AND γ-THIOPYRONES, THEIR USE AS MEDICAMENTS AND PROCESS FOR PREPARING SAME

[75] Inventors: Lutz Müller-Kuhrt, Berlin; Andreas Immelmann, Dusseldorf, both of Germany

[73] Assignees: Analyticon Gesellschaft fur Chemische Analytik und Consulting GmbH, Berlin; Diagen Institut fur Molekularbiologische Diagnostik GmbH, Hilden, both of Germany

[21] Appl. No.: 571,027

[22] Filed: Dec. 12, 1995

Related U.S. Application Data

[63] Continuation of Ser. No. 105,971, filed as PCT/EP92/00062, Jan. 15, 1992, abandoned.

[30] Foreign Application Priority Data

Feb. 8, 1991 [DE] Germany ................ 41 03 904.1

[51] Int. Cl.$^6$ ................ A61K 31/35
[52] U.S. Cl. ................ 514/460; 549/417
[58] Field of Search ................ 549/417; 514/460

[56] References Cited

PUBLICATIONS

K. Yano et al., "Actinopyrones A, B and C, new physiologically active substances. II. Physicochemical properties and chemical structures", Chemical Abstracts, vol. 105, 2261232 (1986).

Mitsui Toatsu Chemicals, "Pyrone derivatives", Chemical Abstracts, vol. 94, 15568f (1981.

Zdero et al., Phytochemistry, 26, 187–190 (1987).

Jaensch et al, ibid, 28, 3497–3501 (1989).

*Primary Examiner*—Nicky Chan
*Attorney, Agent, or Firm*—Jacobson, Price, Holman & Stern, PLLC

[57] ABSTRACT

The invention relates to novel γ-pyrones, γ-pyridones and γ-thiopyrones and their use as medicaments against viral diseases, preferably for the treatment of retroviral diseases, comprising compounds of the formula (I), in which $R_1$ and $R_2$ stand for hydrogen, a branched-chain or unbranched-chain $C_1$ to $C_{26}$, preferably $C_1$ to $C_6$ alkyl, $C_1$ to $C_{26}$ alkenyl or $C_1$ to $C_{26}$ alkinyl group or combinations thereof; $R_3$ stands for a branched-chain or unbranched-chain $C_1$ to $C_{26}$ alkyl group; and $R_4$ stands for a $C_3$ to $C_{26}$ cycloalkyl, branched-chain or unbranched-chain alkyl, alkenyl or alkinyl group. The hydrogen atoms of the methylenic group in $R_1$, $R_2$ and $R_4$ may be substituted by O alkyl ($C_1$ to $C_6$), O acyl, O aryl, O aralkyl and alkyl ($C_1$ to $C_6$) groups, and in $R_4$ also by halogenated groups, oxo groups and hydroxylic groups with double links. The elements represented by Z are independently from each other O, S or NH.

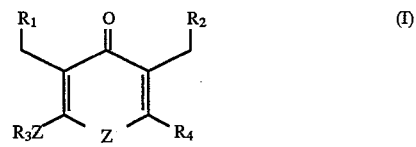

8 Claims, 1 Drawing Sheet

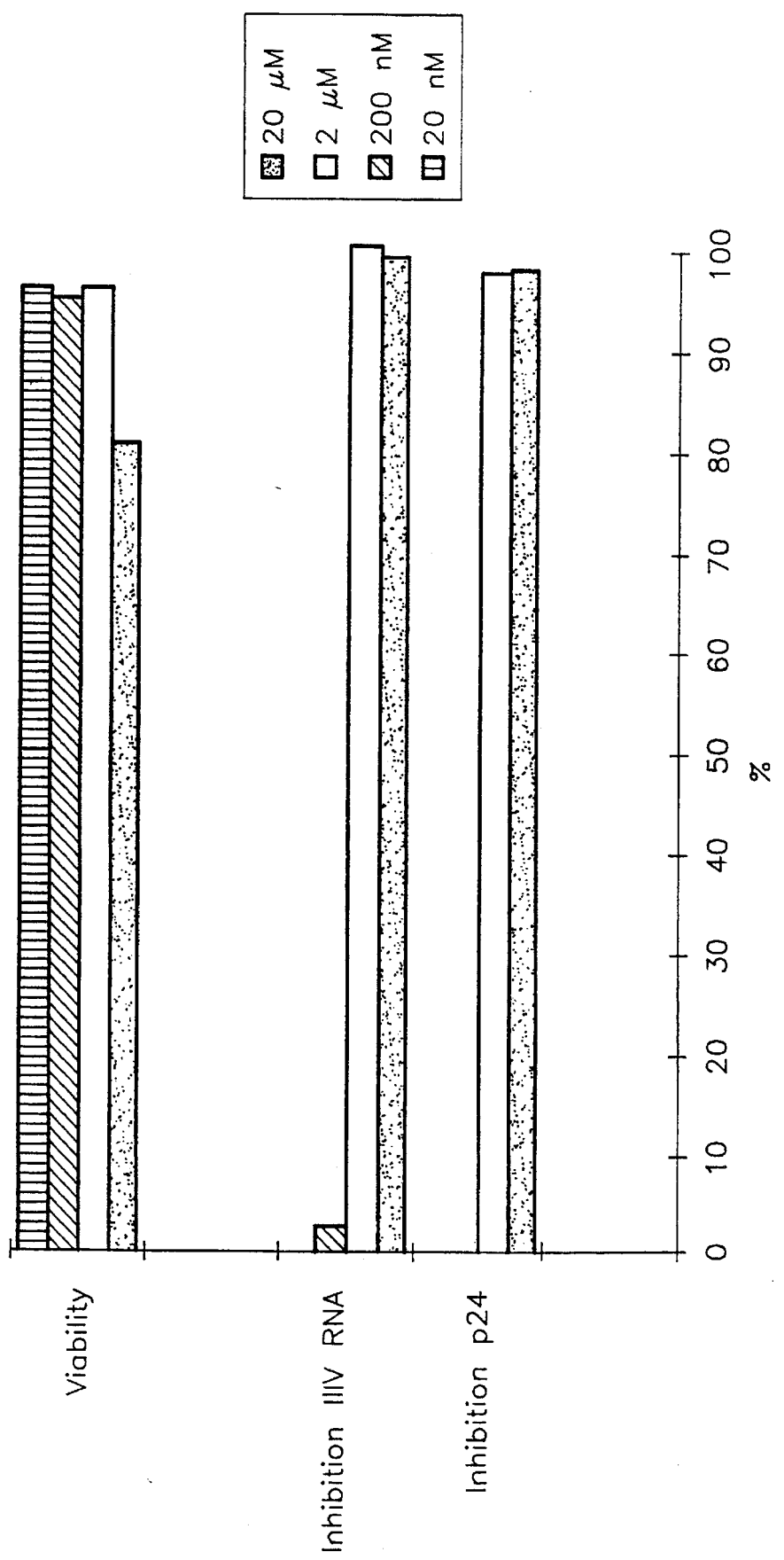

γ-PYRONES, γ-PYRIDONES, AND γ-THIOPYRONES, THEIR USE AS MEDICAMENTS AND PROCESS FOR PREPARING SAME

This application is a continuation of application Ser. No. 08/105,971, filed Aug. 6, 1993, now abandoned; which is a continuation under 35 USC §120 and §365(c) of international application PCT/EP92/00062, filed Jan. 15, 1992.

This invention relates to novel γ-pyrones, γ-pyridones, and γ-thiopyrones, and their use as medicaments for the treatment of viral diseases.

Virus diseases such as hepatitis B and C or AIDS are spreading exponentially. Consequently, the development of antiviral agents has gained great economical importance and pharmaceutical research has focussed thereon. Current antiviral medicaments are characterized by poor antiviral activity spectrum and, in most cases, high toxicity. As severe drawbacks, poor applicability and rapid induction of resistant virus strains are noted.

As antiviral prophylactic agents. Amantadine and Rimantadine are available against influenza viruses, and Metisazone against smallpox viruses. Amantadine and Rimantadine have low toxicity. As further antiviral agents, Idoxuridine, trifluorothymidine, ethyldeoxyuridine, and iododeoxycytidine are known which, particularly with some local herpes infections, can be applied in topical fashion only. However, some of these substances are highly toxic.

Adenine arabinoside and cytosine arabinoside exhibit pronounced immunosuppressive action as well as extensive side effects. For example, they give rise to chromosomal changes.

Bromovinyldeoxyuridine has good activity against herpes simplex virus type 1 and some other viruses but none against herpes simplex virus type 2. Likewise, Acyclovir shows good activity against some herpes viruses but none against cytomegalovirus.

Dihydroxypropoxymethylguanine has activity against Epstein-Barr virus and cytomegalovirus but is very toxic.

Phosphonoformate, Suramin, and Zidovudin show activity against HIV, among others, but have high toxicity.

Many of the above-mentioned substances are active against a viral thymidine kinase, a viral polymerase, or a viral reverse transcriptase. With many of these substances, it has been observed that infecting viruses became resistant even during therapy.

Most recently, polyanions such as dextran sulfate and pentosan polysulfate have proven to be useful substances, since they appear to affect specifically the reverse transcriptase of retroviruses, especially HIV. Thus, German Published Application DE-OS 36 01 136 describes the use of organic polymers containing inorganic anionic groups for prophylaxis and therapy of retroviral infections in mammals.

European Published Application EP-OS 0,293,826 describes therapeutic and prophylactic activity of sulfated polysaccharides against AIDS.

The technical problem of the invention is to provide an antiviral agent having low toxicity, high specific activity, good applicability, and lowest possible tendency to induce resistant virus strains.

This problem is solved by using compounds of formula (I)

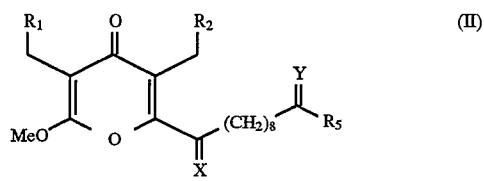

wherein $R_1$ and $R_2$ are H, a branched or unbranched $C_1$ to $C_{26}$ alkyl group, preferably $C_1$ to $C_6$, a $C_1$ to $C_{26}$ alkenyl or $C_2$ to $C_{26}$ alkynyl group or combinations thereof, $R_3$ is a branched or unbranched $C_1$ to $C_{26}$ alkyl group, and $R_4$ is a $C_3$ to $C_{26}$ cycloalkyl, branched or linear alkyl, alkenyl or alkynyl group, and the hydrogen atoms of the methylene groups in $R_1$, $R_2$ and $R_4$ may be replaced by O-alkyl ($C_1$ to $C_6$), O-acyl, O-aryl, O-aralkyl, and alkyl ($C_1$ to $C_6$) groups, and in $R_4$ additionally by halogeno groups, double-bonded oxo groups and hydroxy groups, and each Z independently is O, S or NH, and when $R_1$ is H, $R_2$ is not H, and when $R_2$ is H, $R_1$ is not H and the following compounds are excluded

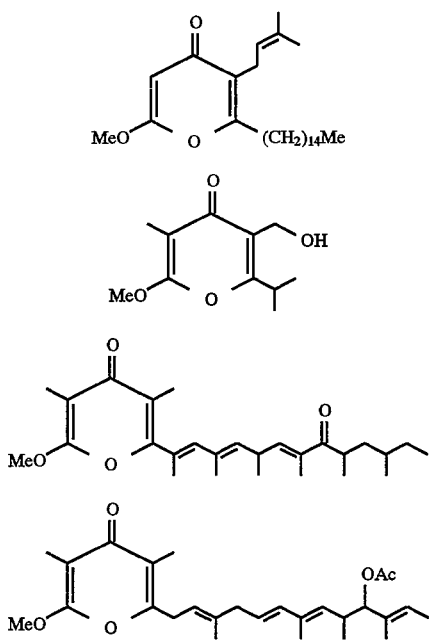

| No. | $R_1$ | $R_2$ | $R_5$ | X | Y |
|---|---|---|---|---|---|
| 1 | H | H | Me | $H_2$ | $H_2$ |
| 2 | H | H | H | $H_2$ | $H_2$ |
| 3 | H | H | Me | $H_2$ | H,OAc |
| 4 | Me | H | Me | $H_2$ | =O |
| 5 | Me | H | Me | $H_2$ | H,OH |
| 6 | Me | H | Me | $H_2$ | H,OAc |
| 7 | Me | Me | Me | $H_2$ | H,OAc |
| 8 | H | H | $CH_2OAc$ | H | $H_2$ |
| 9 | H | H | Me | $H_2$ | =O |
| 10 | Me | H | H | $H_2$ | $H_2$ |
| 11 | Me | H | Me | $H_2$ | $H_2$ |
| 12 | H | H | H | =O | $H_2$ |
| 13 | H | H | Me | =O | $H_2$ |
| 14 | Me | H | H | =O | $H_2$ |
| 15 | Me | H | Me | =O | $H_2$ | where Me means methyl, and the following compounds likewise are excluded

-continued

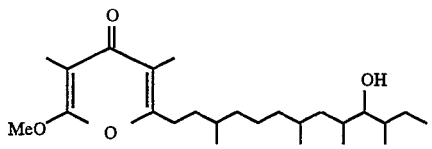
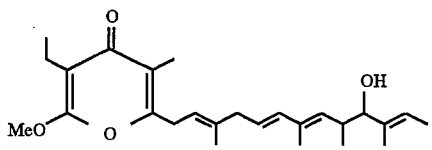
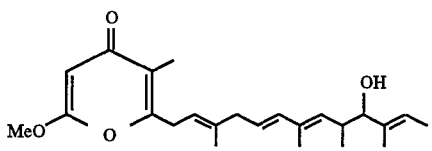
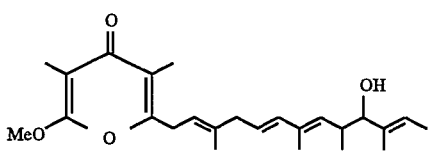
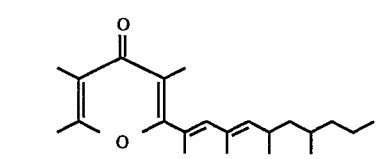
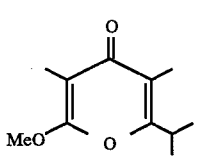
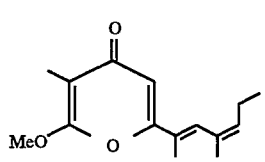
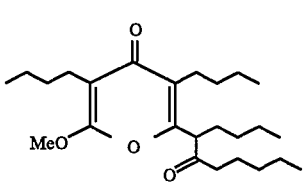
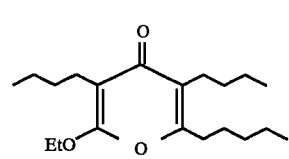
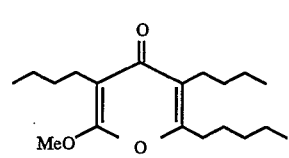

-continued

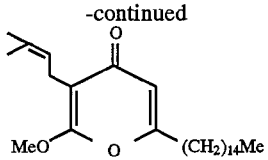
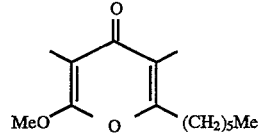

Furthermore, this problem is solved by using in animals in need thereof effective antiviral amount of medicaments containing the compound of formula (I), wherein $R_1$ to $R_4$ and Z have the same meaning as described above.

In a useful embodiment, compounds of formula (II)

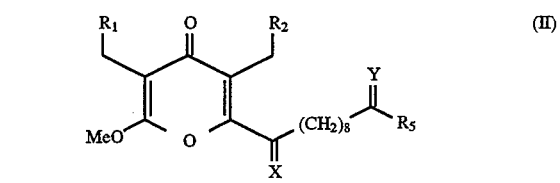

of the γ-pyrone type are used as the compounds contained in medicaments, wherein $R_1$, $R_2$, $R_5$, X, and Y represent the following:

| No. | $R_1$ | $R_2$ | $R_5$ | X | Y |
|---|---|---|---|---|---|
| 1 | H | H | Me | $H_2$ | $H_2$ |
| 2 | H | H | H | $H_2$ | $H_2$ |
| 3 | H | H | Me | $H_2$ | H,OAc |
| 4 | Me | H | Me | $H_2$ | =O |
| 5 | Me | H | Me | $H_2$ | H,OH |
| 6 | Me | H | Me | $H_2$ | H,OAc |
| 7 | Me | Me | Me | $H_2$ | H,OAc |
| 8 | H | H | $CH_2OAc$ | H | $H_2$ |
| 9 | H | H | Me | $H_2$ | =O |
| 10 | Me | H | H | $H_2$ | $H_2$ |
| 11 | Me | H | Me | $H_2$ | $H_2$ |
| 12 | H | H | H | =O | $H_2$ |
| 13 | H | H | Me | =O | $H_2$ |
| 14 | Me | H | H | =O | $H_2$ |
| 15 | Me | H | Me | =O | $H_2$ |

These compounds may be used in the preparation of medicaments for the treatment of viral diseases, preferably retroviral diseases in mammals.

γ-Pyrone derivatives can be obtained starting from dehydroacetic acid via methyl 3,5-dioxohexanoate. Dehydroacetic acid is formed from correspondingly substituted acetoacetic acid derivatives. Dehydroacetic acid is reacted with magnesium methanolate to yield a correspondingly substituted methyl 3,5-dioxohexanoate which can be further derived by, for example, alkylation at CH acidic positions. This is followed by a recyclization step. Preferably, DBU is used as the cyclization reagent. In this fashion, modifying the side chain results in corresponding types of structures (F. Wangemann, Ph.D. Thesis Berlin, 1989, "Synthese von γ-Pyronen aus Podolepis hieracioides").

γ-Pyrone structures lacking an alkoxy function are obtained by condensation of carboxylic acids or derivatives thereof (A. N. Sagredos et al., Liebigs Ann. Chem. 706, 90–94, Vol. 697, pp. 111–115). Canadian Journal of Chemistry, 56, 1796–1799 (1978) describes methods for alkylating pyronones constituting the starting materials for the structures as claimed according to the invention.

Tetrahedron Lett.(1976) 2167, and, for instance, J. Org. Chem. 43, 4966 (1978), describe the preparation of thiopyrane-4-thio-derivatives. In Liebigs Ann. Chem. (1982), pp. 1466–1477, G. Voss and H. Gerlach describe the synthesis of nitrogen-analogous pyrones by reacting the corresponding pyrones with ammonia in methanol by heating in a sealed glass tube.

The preparation of compounds of formula (I) may also be effected by isolating compound (II) from species of the Australian Podolepis plant, especially from *Podolepis longipedata A* and from the roots of *Podolepis rugata* as well as from *Podolepis hieracioides*. The substances are recovered by extraction in organic solvents and subsequent purification and extract work-up using chromatography. According procedures are described in F. Bohlmann et al., Phytochemistry, Vol. 26, pp. 187–190 (1987), and J. Jakupovic et al., Phytochemistry, Vol. 28, pp. 3497–3501 (1989).

The substances obtained in this fashion are tested for antiviral activity in a test system. As the test system, determination of virus replication in HIV-infected blood cells was used. The system permits the detection of antiviral substances interfering with virus replication and infective potential. Such substances might prevent virus particles from invading the cell interior, and thus, viruses having proliferated within previously infected cells were no longer capable of finding new target cells. In this way, effective prophylaxis against viral diseases was possible, and a therapy could be initiated where virus invasion into the cell interior is prevented. As a consequence, the infection would be stopped and the aim of therapy attained rapidly and simply. One might think of further intracellular sites of action for antiviral agents as, for example, the so-called uncoating or the expelling of infective virions.

The antiviral test system is designed such that it indicates, for the model virus (HIV), all of the substances having antiviral activity while molecular site or mechanism of action are not known. The strong point of the test system is founded in its sensitivity, specificity and broad spectrum of possible target sites for antiviral substances. Thus, the test system indicates protease inhibitors as well as RT inhibitor substances or blockers of virus reception by the host cell. Likewise, active substances reaching beyond the class of viruses such as polyanions with their broad activity spectrum are detected reliably. High sensitivity is ensured by using non-transformed human peripheral blood cells.

The system is especially suited for detecting new classes of antivirus-active substances having so-called leading structures, i.e., a basic structural pattern, the chemical derivatives of which have influence upon pharmacological—in this case—antiviral properties. Then, leading structures are the basis for a purposeful synthesis of these derivatives.

In this test, the γ-pyrones according to the invention were remarkable for their antiviral activity. At a concentration of 10 μmol which is less than the tenth part of the half-maximum cytotoxic concentration, reduced HIV replication was observed four days after exposition of human lymphocytes to HIV. Thus, a new class of antiviral substances has been surprisingly discovered, the common basic structural feature of which being the γ-pyrone structure.

Embodiment:

The γ-pyrones of table 1 were recovered from Australian *Podolepis heracioides* by extraction and were subsequently purified by chromatography.

TABLE 1

| No. | $R_1$ | $R_2$ | $R_5$ | X | Y | Activity |
|---|---|---|---|---|---|---|
| 1 | H | H | Me | $H_2$ | $H_2$ | + |
| 2 | H | H | H | $H_2$ | $H_2$ | + |
| 3 | H | H | Me | $H_2$ | H,OAc | ++ |
| 4 | Me | H | Me | $H_2$ | =O | ++ |
| 5 | Me | H | Me | $H_2$ | H,OH | + |
| 6 | Me | H | Me | $H_2$ | H,OAc | + |
| 7 | Me | Me | Me | $H_2$ | H,OAc | + |
| 8 | H | H | $CH_2OAc$ | H | $H_2$ | – |
| 9 | H | H | Me | $H_2$ | =O | + |
| 10 | Me | H | H | $H_2$ | $H_2$ | – |
| 11 | Me | H | Me | $H_2$ | $H_2$ | + |
| 12 | H | H | H | =O | $H_2$ | – |
| 13 | H | H | Me | =O | $H_2$ | + |
| 14 | Me | H | H | =O | $H_2$ | + |
| 15 | Me | H | Me | =O | $H_2$ | + |

Table 1 shows the recovered substances as well as their antiviral activity which was measured as follows:

Substance-induced inhibition of HIV proliferation in cell culture is determined by quantitative determination of a viral structure protein (p24) and viral nucleic acid (HIV RNA). A culture of human lymphocytes is used for virus proliferation.

Subsequent to preparation of a 10 mM solution, the substance to be tested is adjusted by serial 1:10 dilutions in the culture medium to a non-toxic concentration established in approximation in a previous cytotoxicity test. Human lymphocytes are isolated from donor blood, with the lymphocytes being recovered from the buffy coats of the blood containers by density gradient centrifugation.

In a safety lab meeting the L3 guidelines, the cells are infected with human immunodeficiency virus (HIV). Subsequently, the infected cells are incubated in presence of the substance to be tested for four days at 37° C. under water vapor-saturated atmosphere containing 5% $CO_2$.

The concentration of HIV-specific core protein p24 being secerned into the culture supernatant by the virus-producing cells after infection of the lymphocytes is determined by a "Sandwich Elisa" Test, with evaluation being done photometrically. The protein p24 concentration is calculated from a calibration curve as well as from the resulting absorption values delivered by the cultures of HIV-infected lymphocytes having grown in presence of the substance to be examined. Substance-induced inhibition of p24 production is calculated in percentage by comparison with an untreated control culture.

HIV RNA having formed within the infected lymphocytes is detected by nucleic acid hybridization, with evaluation being done photometrically. The concentration of HIV RNA is calculated from a calibration curve as well as from the resulting absorption values delivered by the cultures of HIV-infected lymphocytes having grown in presence of the substance to be examined. Substance-induced inhibition of HIV RNA production is calculated in percentage by comparison with an untreated control culture.

Viability of the infected cells is determined by the trypan blue technique. Infected cells cultivated for four days in presence of the substances to be examined are treated with a solution of trypan blue. The proportion of blue-colored dead cells is determined in a microscopical analysis by counting. The viability results from the difference of total cells and dead cells and is similarly given in percent.

FIG. 1 illustrates the dose/activity relationship for inhibition of protein 24, inhibition of HIV RNA, and viability for compound 4 of table 1.

Table 2 illustrates the effect of compounds 3, 4, 6, and 7 according to table 1 on various isolated HIV materials in comparison to azidothymidine (AZT) and tetrahydroimidazolbenzodiazepine (TIBO) as well-established active substances against HIV.

TABLE 2

| Compound | Concentr. | HIV-1 Standard (day 3, ng p24/ml) | HIV-1 AZT Resist. (day 3, ng p24/ml) | HIV-2 (day 4, pg RNA/ml) |
|---|---|---|---|---|
| Control | 0 | 55.7 | 48.9 | 333 |
| AZT | 100 ng/ml | 0 | 21.0 | 0 |
|  | 10 ng/ml | 15.9 | 43.2 | 141 |
|  | 1 ng/ml | 37.6 | 47.1 | 298 |
|  | 0.1 ng/ml | 58.8 | 47.9 | 283 |
| TIBO | 100 nM | 0 | 42.9 | 583 |
|  | 10 nM | 7.2 | 46.8 | 465 |
|  | 1 nM | 18.5 | 46.2 | 376 |
|  | 0.1 nM | 46.5 | 45.7 | 370 |
| 3 | 10 μM | n.d. | 13.9 | 0 |
| 4 | 10 μM | n.d. | 4.1 | 0 |
| 6 | 10 μM | n.d. | 46.7 | 27 |
| 7 | 10 μM | n.d. | 51.5 | 16 | n.d. = not determined

Activity of the compounds listed in table 2 against isolated HIV 1 material that was isolated from a patient who had been treated with AZT for 18 months was measured. Using in-vitro tests, this isolated material shows significant resistance towards reverse transcriptase inhibitors, two of which were carried along as reference substances in the present test, namely, azidothymidine (AZT) as a nucleoside analogue and tetrahydroimidazolbenzodiazepine (TIBO) as a non-nucleoside analogue inhibitor of reverse transcriptase. Furthermore, activity of these compounds against isolated HIV 2 material was examined. Correspondingly, AZT and TIBO were carried along as reference substances, with TIBO, as is known, having selective activity for isolated HIV 1 material as also can be seen from the measured data.

Table 2 unambiguously indicates that compounds 3, 4, 6, and 7 according to table 1 inhibit virus replication both in cells infected with HIV 2 and in cells infected with an AZT-resistant isolated material.

What is claimed is:

1. An anti-viral medicament comprising an effective anti-viral amount of a compound having the formula:

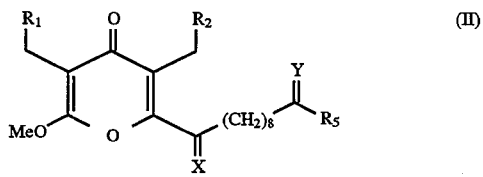

(II)

wherein $R_1$, $R_2$, $R_5$, X, and Y are defined as follows:

| No. | $R_1$ | $R_2$ | $R_5$ | X | Y |
|---|---|---|---|---|---|
| 1 | H | H | Me | $H_2$ | $H_2$ |
| 2 | H | H | H | $H_2$ | $H_2$ |
| 3 | H | H | Me | $H_2$ | H, OAc |
| 4 | Me | H | Me | $H_2$ | =O |
| 5 | Me | H | Me | $H_2$ | H, OH |
| 6 | Me | H | Me | $H_2$ | H, OAc |
| 7 | Me | Me | Me | $H_2$ | H, OAc |
| 8 | H | H | Me | =O | $H_2$ |
| 9 | Me | H | H | =O | $H_2$ |
| 10 | Me | H | Me | =O | $H_2$ | together with a pharmaceutically acceptable carrier.

2. The medicament of claim 1 obtained by extraction from an Australian Podolepis plant and subsequent purification.

3. The medicament of claim 2 wherein the Podolepis plant is P. longipedata A.

4. The medicament of claim 2 wherein the Podolepis plant is a root of P. rugata or P. hieracioides.

5. A method of treating a viral infection comprising administering to a mammal in need thereof the medicament of claim 1.

6. A method of treating a viral infection comprising administering to a mammal in need thereof the medicament of claim 2.

7. A method of treating a viral infection comprising administering to a mammal in need thereof the medicament of claim 3.

8. A method of treating a viral infection comprising administering to a mammal in need thereof the medicament of claim 4.

* * * * *